United States Patent
Sampson et al.

(10) Patent No.: US 6,743,184 B2
(45) Date of Patent: *Jun. 1, 2004

(54) SYSTEM AND METHOD FOR DETECTING PERFORATIONS IN A BODY CAVITY

(75) Inventors: Russel M. Sampson, Mountain View, CA (US); Mike O'Hara, Flagstaff, AZ (US); Csaba Truckai, Saratoga, CA (US); Dean T. Miller, Menlo Park, CA (US)

(73) Assignee: Novacept, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/400,823

(22) Filed: Mar. 27, 2003

(65) Prior Publication Data

US 2003/0191412 A1 Oct. 9, 2003

Related U.S. Application Data

(63) Continuation of application No. 09/710,102, filed on Nov. 10, 2000, now Pat. No. 6,554,780.
(60) Provisional application No. 60/164,482, filed on Nov. 10, 1999.

(51) Int. Cl.$^7$ .......................... A61B 5/00; A61M 31/00
(52) U.S. Cl. ................ 600/560; 600/587; 600/561; 607/63; 606/41
(58) Field of Search ............................ 600/560–562, 600/587, 591, 593, 101, 156, 158, 104, 105, 135, 153; 606/27, 40, 37, 41, 45, 46, 49; 607/63, 96, 101, 105, 113, 115, 116, 138; 604/20, 23, 26, 27, 65–67, 114, 118, 500, 515, 920

(56) References Cited

U.S. PATENT DOCUMENTS

| | | | |
|---|---|---|---|
| 4,611,602 A | 9/1986 | Bolduc | |
| 4,735,603 A | 4/1988 | Goodson et al. | |
| 4,971,034 A | 11/1990 | Doi et al. | |
| 5,084,044 A | * 1/1992 | Quint | 606/27 |
| 5,098,375 A | 3/1992 | Baier | |
| 5,152,745 A | 10/1992 | Steiner et al. | |
| 5,191,898 A | 3/1993 | Millar | |
| 5,360,396 A | 11/1994 | Chan | |
| 5,439,441 A | 8/1995 | Grimsley et al. | |
| 5,769,880 A | 6/1998 | Truckai et al. | |
| 5,800,381 A | 9/1998 | Ognier | |
| 5,891,134 A | 4/1999 | Goble et al. | |
| 5,891,136 A | 4/1999 | McGee et al. | 606/41 |
| 5,951,497 A | 9/1999 | Wallace et al. | |
| 6,057,689 A | 5/2000 | Saadat | |
| 6,066,132 A | * 5/2000 | Chen et al. | 606/28 |
| 6,159,160 A | 12/2000 | Hsei et al. | |
| 6,179,835 B1 | * 1/2001 | Panescu et al. | 606/41 |
| 6,554,780 B1 | * 4/2003 | Sampson et al. | 600/587 |

FOREIGN PATENT DOCUMENTS

DE 43 06 629 A1 9/1994
EP 0 278 217 A1 8/1988

* cited by examiner

*Primary Examiner*—Charles Marmor
(74) *Attorney, Agent, or Firm*—Stallman & Pollock LLP

(57) ABSTRACT

A system and method for detecting perforations in a body cavity. In accordance with the method of the invention, a fluid (liquid or gas) is delivered into a body cavity to slightly pressurize the cavity. A pressure sensing system monitors the pressure within the cavity for a predetermined test period. If cavity pressure is not substantially sustained during the test period, the physician is alerted to further assess the cavity for perforations before initiating treatment within the cavity. In a preferred form of the system, a medical treatment system such as an RF ablation system is provided with perforation detection functionality. The system preferably includes a pre-test lockout that prevents RF power delivery unless a perforation detection procedure previously has been performed.

23 Claims, 5 Drawing Sheets

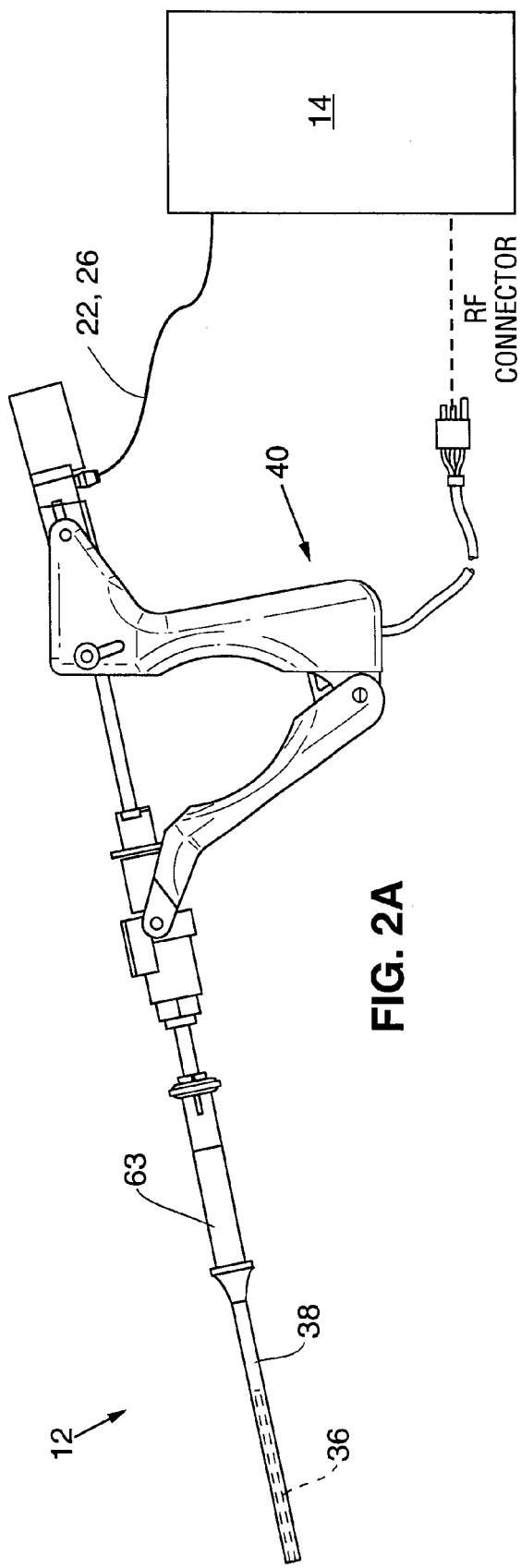

SYSTEM AND METHOD FOR DETECTING PERFORATIONS IN A BODY CAVITY

ORIORITY

This application is a continuation of U.S. application Ser. No. 09/710,102, filed Nov. 10, 2000, now U.S. Pat. No. 6,554,780, which claims priority to U.S. Provisional Application No. 60/164,482, filed Nov. 10, 1999.

FIELD OF THE INVENTION

The present invention relates to the field of systems and methods for detecting the presence of perforations in body cavities. More particularly, the present invention relates to a system and method that pressurizes a body cavity and detects whether the body cavity can maintain a pressurized condition

BACKGROUND OF THE INVENTION

There are certain medical procedures that are carried out within a body cavity. One example of such a procedure is tissue ablation. Ablation of the interior lining of a body organ is a procedure which involves heating the organ lining to temperatures which destroy the cells of the lining or coagulate tissue proteins. Such a procedure may be performed as a treatment to one of many conditions, such as chronic bleeding of the endometrial layer of the uterus or abnormalities of the mucosal layer of the gallbladder. Existing methods for effecting ablation include circulation of heated fluid inside the organ (either directly or inside a balloon), laser treatment of the organ lining, and resistive heating using application of RF energy to the tissue to be ablated.

Ablation procedures are often carried out without direct endoscopic visualization. For example, ablation of the endometrium typically involves insertion of an elongate ablation device into the patient's cervix without the use of a hysteroscope. As can be appreciated, the presence of a perforation in the uterus could result in inadvertent passage of the ablation device through the perforation and out of the uterus into the bowel. Although events of this nature are rare, the injury that could result from such occurrences make it highly desirable to provide a mechanism by which a physician can evaluate whether perforations are present in a body cavity before a treatment device such as an ablation device is used to deliver power.

SUMMARY OF THE INVENTION

The present invention is a system and method for detecting perforations in a body cavity. In accordance with the method of the invention, a fluid (either liquid or gas) is delivered into a body cavity to slightly pressurize the cavity. A pressure sensing system monitors the pressure within the cavity for a predetermined test period. If cavity pressure is not substantially sustained during the test period, the physician is alerted to further assess the cavity for perforations before initiating treatment within the cavity. In a preferred form of the system, a medical treatment system such as an RF ablation system is provided with perforation detection functionality. The system preferably includes a pre-test lockout feature that prevents RF power delivery unless a perforation detection procedure has been performed.

BRIEF DESCRIPTION OF THE DRAWINGS

FIG. 2A is a side elevation view of an ablation device that may be used with the system of FIG. 1.

DETAILED DESCRIPTION

Figure 1:
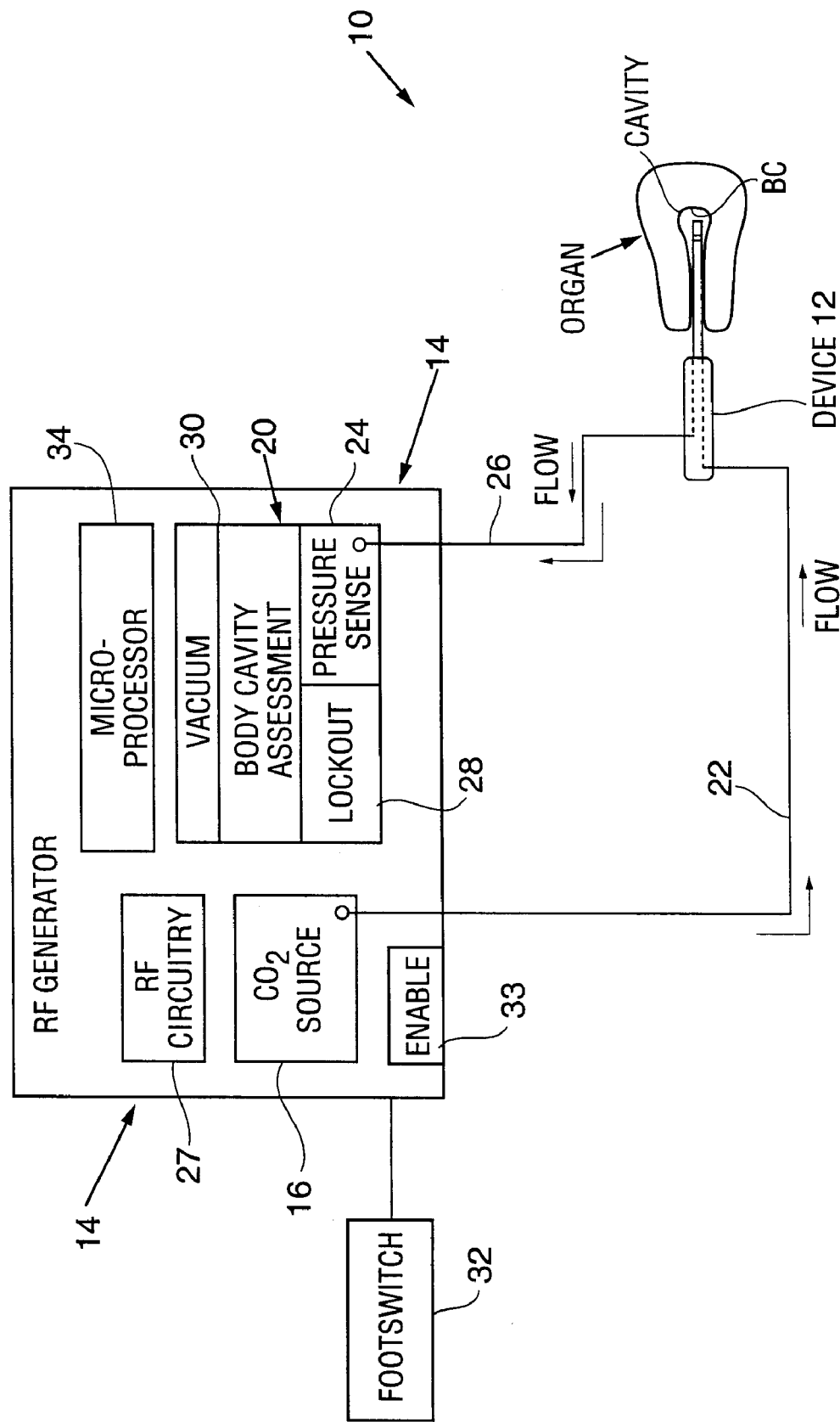
FIG. 1 is a schematic representation of a perforation detection system utilizing principles of the present invention.

A perforation detection system 10 (also referred to as a "body cavity assessment system") utilizing principles of the present invention will be described herein as forming part of an RF ablation system used to ablate tissue within a body cavity such as a uterus. However, it should be appreciated that the perforation detection system 10 may be provided with another type of system used for treatment, or it may be provided independently of a larger treatment system.

Generally speaking, perforation detection system 10 includes a medical ablation device 12 of a type used for tissue ablation, and an RF generator system 14 of the type used to deliver RF ablation energy to an electrode array on ablation device 12. The RF generator unit, however, is provided with additional components that are used for the body cavity assessment function of the present invention. In particular, the RF generator unit is provided with a fluid/gas source 16 and a body cavity assessment system 20. Fluid/gas source 16 is fluidly coupled to ablation device 12 via a source line 22. The ablation device is positionable within a body cavity BC so as to deliver fluid/gas from source 16 through the source line 22 and the ablation device and into the body cavity.

Body cavity assessment system 20 includes a pressure sensing system 24 fluidly coupled to the medical device via pressure detection/signal line 26. Pressure sensing system 24 monitors the pressure within the body cavity BC while fluid/gas is being (or after it has been) delivered to the body cavity, and detects whether elevated pressure can be maintained above a predetermined threshold level over a predetermined period of time. If it cannot, the user is alerted that there may be a perforation in the organ.

Body cavity assessment system 20 further includes a lockout system 28 that prevents treatment with the ablation device 12 unless body cavity assessment has been performed (pre-test lockout) and that prevents treatment if the body cavity assessment indicates a possible perforation (post-test lockout). The RF generator system 14 is additionally provided with a vacuum system 30 coupled to pressure detection/signal line 26, RF circuitry 27, and other components needed to perform the ablation function. A footswitch 32 or other input device controls operation of the RF generator system 14. A microprocessor or programmable logic device 34 within the RF generator system 14 governs various functions, including the body cavity assessment, lockout, and RF ablation procedures.

Ablation Device

Figure 2B:
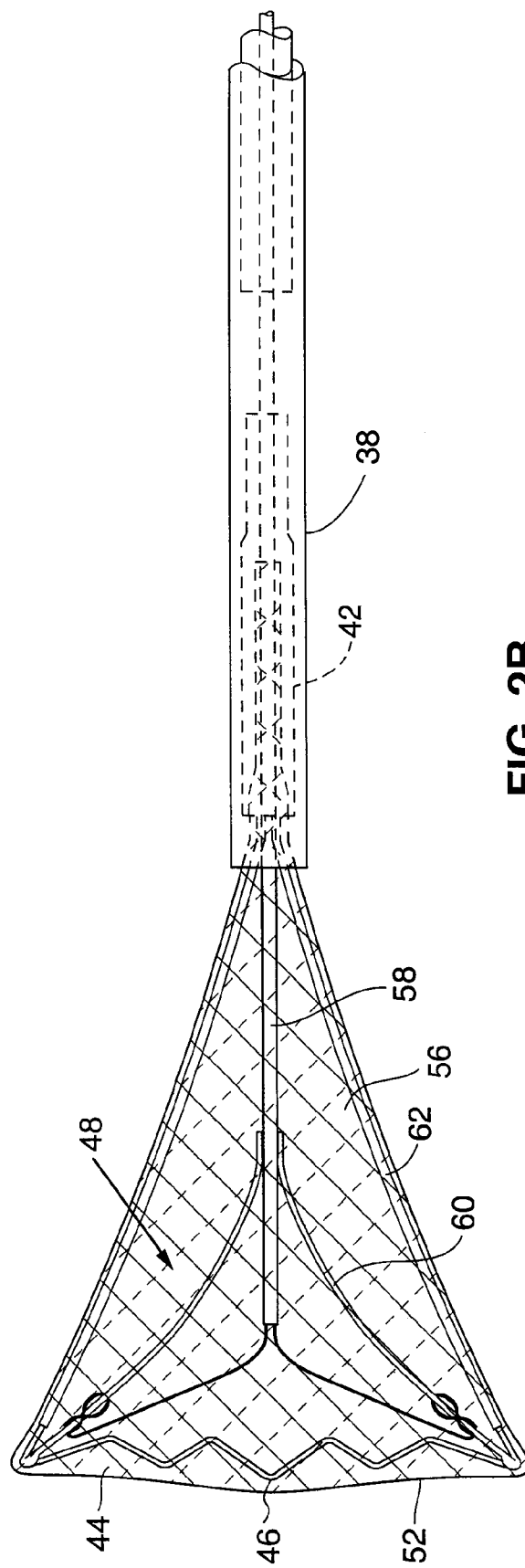
FIG. 2B is a plan view of the RF applicator head of the ablation device of FIG. 2A.

An example of an RF ablation device 12 that may be used with the system 10 is shown in FIG. 2A and 2B. Ablation devices of this type are shown and described in U.S. Pat. No. 5,769,880 and U.S. application Ser. No. 09/103,072, each of which are incorporated herein by reference. A similar device is the NovaSure® ablation device available from Novacept, Inc., Palo Alto, Calif. Naturally the perforation detection system may be provided in combination with the other medical devices as well. Such alternative devices include thermal ablation devices in which heated liquid is circulated through a balloon positioned within the body cavity of interest, or other device used for procedures besides ablation. Alternatively, the system may be provided with two medical devices, one for use in delivering inflation medium and another for use in treating body tissue. As a further alternative, a treatment device may be provided independent of the system 10.

Ablation device 12 is configured to deliver RF ablation energy to the interior surface of a body cavity, while causing moisture (e.g. steam) generated during ablation to be withdrawn away from the body tissue—preferably using suction. This moisture transport feature of the device 12 is advantageous in that removing steam from the ablation site minimizes the amount of thermal ablation that would otherwise be caused by the steam. Greater control over ablation depth is thus achieved by allowing ablation to occur only (or primarily) by RF energy rather than by thermal conduction.

The device 12 includes an RF applicator head 36, a sheath 38, and a handle 40. The applicator head 36 is slidably disposed within the sheath 38 to give the applicator head 36 a streamlined profile (FIG. 2A) to facilitate insertion of the device into a body cavity (e.g. the uterine cavity). Once the applicator head 36 has been inserted into the body cavity, handle 40 is manipulated to cause the applicator head 36 to extend from the distal end of the sheath 38 and to expand into the position shown in FIG. 2B as to make contact with body tissue.

Referring to FIG. 2B, applicator head 36 extends from the distal end of a length of tubing 42 which is slidably disposed within the sheath 38. Applicator head 36 includes an external electrode array 44 and an internal deflecting mechanism 46 used to expand and tension the array for positioning into contact with the tissue.

The array 44 is preferably formed of a stretchable metallized fabric mesh which is preferably knitted from a nylon and spandex knit plated with gold or other conductive material. In one array design, the knit is formed of three monofilaments of nylon knitted together with single yarns of spandex. Each yarn of spandex has a double helix of five nylon monofilaments coiled around it.

When in its expanded state, the array 44 includes a pair of broad faces 48 (one of which is shown in FIG. 2B) spaced apart from one another, and narrower side faces (not shown) extending between the broad faces 48 along the sides and distal end of the applicator head 36, and a distal face 52 extends between the broad faces 48 at the distal end of the applicator head 36.

Insulating regions (not shown) formed by etching or other techniques on the applicator head divide the mesh into electrode regions.

The array may be divided by the insulated regions into a variety of electrode configurations. In a preferred configuration the insulating regions divide the applicator head into four electrodes by creating two electrodes on each of the broad faces.

Deflecting mechanism 46 and its deployment structure is enclosed within electrode array 44. External hypotube 58 extends from tubing 42 and an internal hypotube 60 is slidably and co-axially disposed within hypotube 58. Flexures 62 extend from the tubing 42 on opposite sides of external hypotube 58. Hypotube 60 is a dual lumen tube that is coupled to the pneumatic subsystem as will be described below.

A plurality of longitudinally spaced apertures (not shown) are formed in each flexure 62. During use, these apertures allow moisture to pass through the flexures and to be drawn into the exposed distal end of hypotube 58 using a vacuum source located in the RF generator system 14 and fluidly coupled to hypotube 58.

Each flexure 62 preferably includes conductive regions that are electrically coupled to the array 44 for delivery of RF energy to the body tissue. For example, strips of copper tape (not shown) or other conductive material may extend along opposite surfaces of each flexure. Conductor leads (not shown) are electrically coupled to the strips and extend through tubing 42 to an electrical cable which is attachable to the RF generator.

During use of the ablation device, the applicator head 36 is inserted into the uterus with the sheath 38 covering the array 44 to compress the applicator head 36 into a streamlined condition. Once the applicator head is within the uterus, the handle is used to withdraw the sheath and to open the array into its deployed position. Vacuum source 30 (FIG. 1) is activated, causing application of suction to hypotube 60. Suction helps to draw uterine tissue into contact with the array 44.

Ablation power is supplied to the electrode array 44 by the RF generator system 14. The tissue is heated as the RF energy passes from electrodes 56 to the tissue, causing moisture to be released from the tissue. The vacuum source helps to draw moisture from the uterine cavity into the hypotube 60. Moisture withdrawal is facilitated by the apertures formed in flexures, by preventing moisture from being trapped between the flexures and the lateral walls of the uterus.

Pneumatic Subsystem

Figure 3:
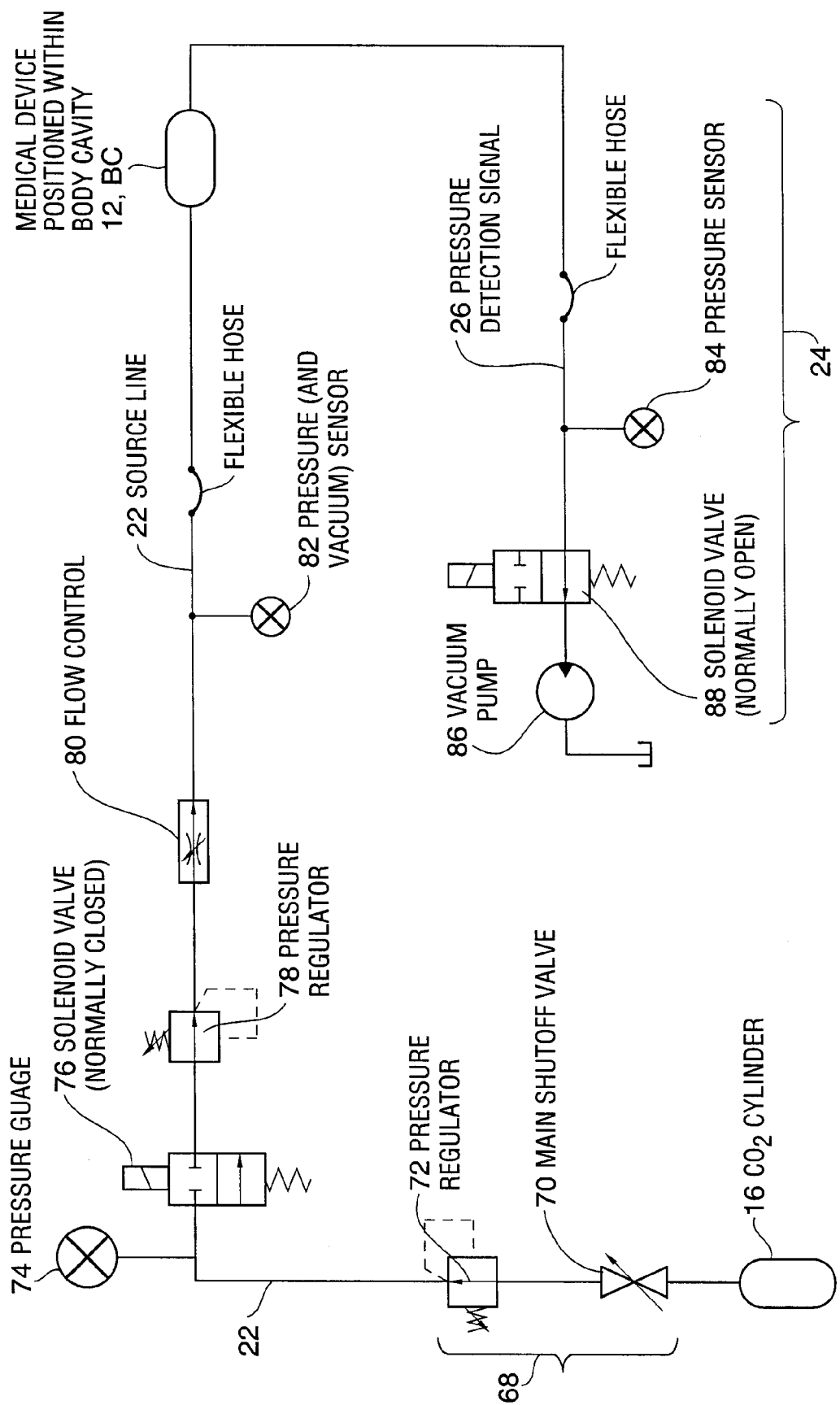
FIG. 3 is a schematic representation of the pneumatic subsystem of the system of FIG. 1.

The fluid/gas source 16, pressure sensing system 24, and associated components are shown in FIG. 3. Each of the components of the pressure sensing system 24 is preferably coupled to microprocessor 34 of the RF generator system 14 although for clarity the microprocessor is not shown in FIG. 3. All pressure transducers, solenoid valves, and the vacuum pump are controlled by the microprocessor. As discussed, a programmable logic device may be used in place of the microprocessor, although the term "microprocessor" will be used here for simplicity.

It is also important to note that in the embodiment described below the two lines (source line 22 and pressure detection/signal line 26) play different roles during RF ablation than for perforation detection. Specifically, the signal line 26 for perforation detection serves as a suction line for ablation. The source line 22 for perforation serves as a vacuum signal line for ablation.

Components along the source line 22 will first be described. Fluid/gas source 16 is preferably a disposable $CO_2$ cylinder, and may be a 16 gm cylinder providing approximately 850 psi at 25 C. One such example is the Linde medical grade 16 gm cylinder. The cylinder is removably attached to a pressure regulator 68 such as the Leland Model 50033 or equivalent. Regulator 68 includes a main shutoff valve 70 and pressure regulation component 72 which has a control pressure of approximately 60 psi. A pressure gauge 74 such as SenSym model ASCX100DN or equivalent is fluidly coupled to source line 22. Pressure gauge 74 monitors the pressure remaining in the fluid/gas source 16 so as to detect when a low volume of fluid/gas remains, or when the user has failed to open the valve 70.

A solenoid valve 76 is positioned along the source line 22, downstream of the pressure regulator 68. Valve 76 remains in a closed condition, preventing flow of gas through the line 22, except when a cavity assessment procedure is being carried out. A second pressure regulator 78, such as an Airtrol R-920 series regulator, is positioned downstream of the valve 76 so as to reduce pressure in line 22 down to approximately 90+/−10 mmHg during a cavity assessment procedure. A flow control orifice 80, positioned downstream of regulator 78, limits flow in line 14 to 100+/−10 scc/min (standard cc/min). A pressure sensor 82 downstream of orifice 80 monitors whether the pressure limit (of, for example, approximately 100 mm Hg) has been exceeded. If the limit has been exceeded, an output signal from this sensor causes an audible alarm to be triggered and the solenoid valve 76 is turned off. Downstream of orifice 80, source line 22 is coupled, using a flexible Tygon® tubing for example, to the introducer sheath 38 (FIG. 2B) of the ablation device 12. The introducer sheath is located at the internal surface of the body cavity BC (the internal os, for example, in the case of a uterine cavity) so as to deliver gas into the body cavity BC that is to be treated.

Turning to the components along the pressure detection line 26, the pressure signal line 26 is fluidly coupled, using a Tygon® tubing for example, to the lumen of hypotube 60. Downstream of the medical device 12 is a pressure sensor 84, such as the SenSym ACSX05DN. During a cavity assessment procedure, sensor 84 monitors pressure in the pressure signal line 26 and delivers the signal to microprocessor 34. Microprocessor 34 (or other electronic means such as the programmable logic device mentioned previously) then determines if pressure in the body cavity BC has failed to achieve a predetermined threshold (indicating a perforation in the body cavity) or if it has and maintained the threshold for a predetermined time period (indicating that the body cavity has no perforation). In this capacity, the microprocessor or (programmable logic device) serves as a feedback means that activates a notification signal to alert a user if the pressure monitored by the pressure sensor fails to rise and remain above a predetermined level during a predetermined amount of time. The microcroprocessor may initiate various forms of notification signals, such as visual or auditory signals.

Further downstream of the pressure sensor 84 is a vacuum pump 86. While not needed for perforation detection, vacuum pump 86 is used to carry out the moisture transport function of the medical device 12 described in the section entitled Ablation Device above.

A second solenoid valve 88 lies upstream of the vacuum pump 86. Valve 88 remains open at all times except during cavity assessment. Because the exhaust line of the vacuum pump may not be air-tight when it is not operating (including during the cavity assessment procedure) the valve 88 is provided to close the pressure signal line against leaks through the vacuum pump.

Figure 4:
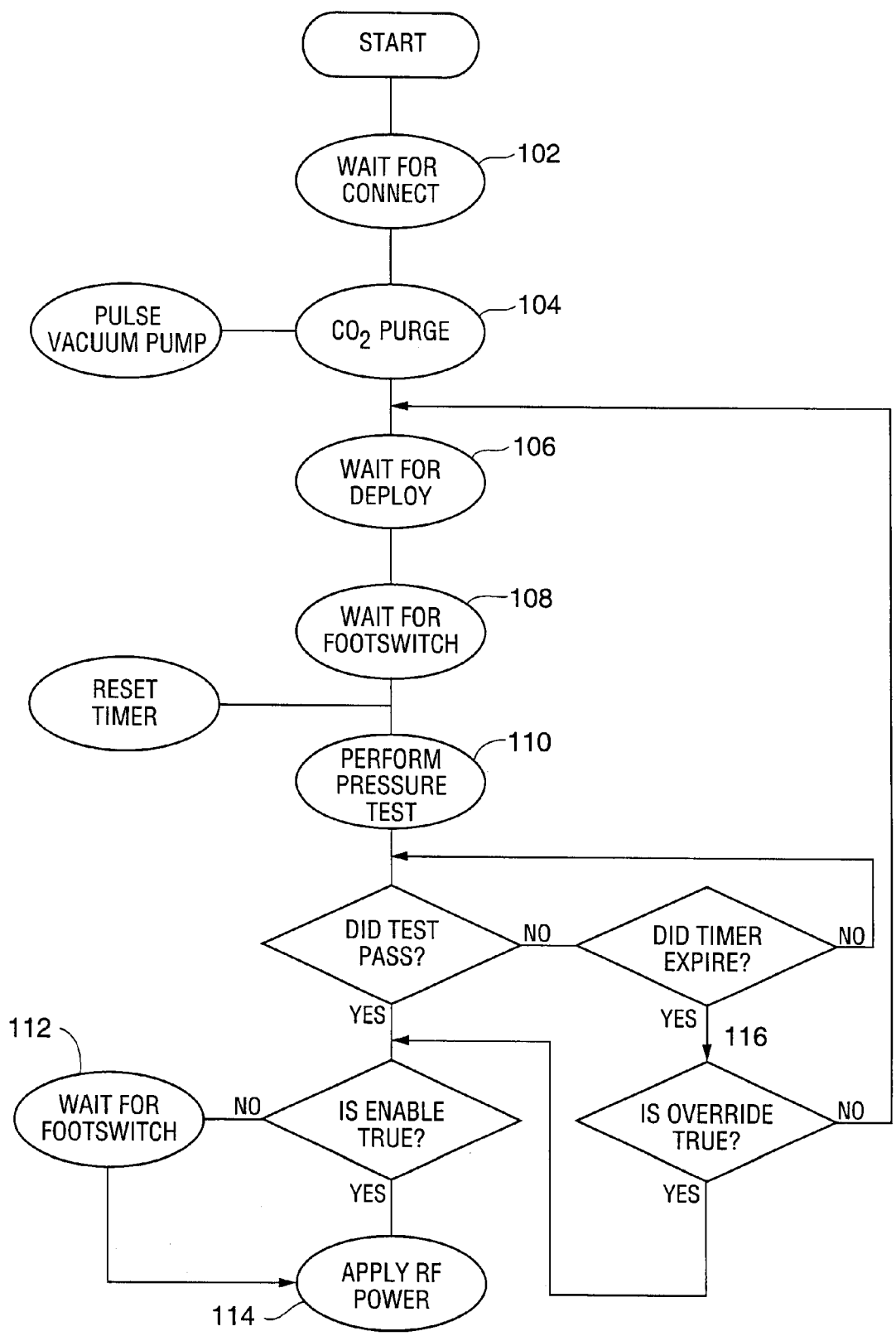
FIG. 4 is a simplified state diagram illustrating a mode of operation utilizing the perforation detection and lockout features of the present invention.

A simplified state diagram illustrating operation of the system is shown in FIG. 4. Operation begins with valve 76 in the closed condition, and with valve 88 in the opened condition. In preparation for use of the system, a CO2 cylinder 16 is connected to the appropriate receiving device on the RF Generator's pneumatic subsystem (FIG. 3). The power to the generator is switched on. Pressure gauge 74 detects the pressure in the portion of pressure/monitoring line 22 extending between $CO_2$ cylinder 16 and valve 76. If the user has failed to open the main $CO_2$ shutoff valve 70, or if the pressure detected by gauge 74 is less than the specified pressure, an audible alert will sound, indicating a low-gas condition. Assuming no low-gas condition is detected, the user will connect the ablation device 12 to the RF generator system 14.

The system remains in a "WAIT FOR CONNECT" condition, step 102, until the user connects the ablation device 12 to the RF generator system. When the ablation device is plugged in, it actuates a microswitch or similar feature, which alerts the microprocessor that the ablation device has been connected. Connection of the device automatically starts the "CO2 PURGE" cycle, step 104. During the purge cycle, valve 76 is opened to permit the flow of $CO_2$ through the device to drive air from the device. The purge cycle lasts for a duration sufficient to purge the air from the system, approximately 10 seconds. During the purging cycle the user is alerted by audible and visual indicators not to insert the device into the body cavity in order to prevent air from being delivered into the body. As a safety precaution, the vacuum pump that is part of the RF Controller is pulsed every few seconds during purging. If the user has inserted the ablation device into a body cavity during purging, the vacuum pump will draw out air that is delivered to the body.

During the purge cycle and device insertion into the body cavity, the ablation device is closed, such that the poles of the electrode array are in contact with each other. A low voltage signal is applied to the ablation device which senses that the poles are in contact by detecting a DC short. After the completion of the purging cycle the system waits for the device to be deployed within the patient, step 106, by monitoring for the end of the DC short condition. Once the user inserts the device into the uterine cavity and opens the array, the system detects that a DC short condition is no longer present. As a safety precaution, the perforation detection cycle cannot be initiated until the DC short condition is eliminated. In this way the last operation to be performed before the application of RF energy is the perforation detection cycle.

From the completion of the purge cycle to the initiation of the perforation detection test, a continuous, low level flow of CO2 is circulated through the ablation device to keep the source and pressure signal lines open and free from blockage.

Next, the system waits for the user to depress the footswitch 32, "WAIT FOR FOOTSWITCH", step 108. Once the footswitch has been depressed, a 30-second timer is initialized ("RESET TIMER") and the perforation detection test, ("PERFORM PRESSURE TEST") 110 begins. Valve 88 is energized to close off the vacuum pump 86 to avoid loss of pressure through it. If it was not already opened, valve 76 is opened, allowing $CO_2$ to flow into the body cavity via medical device 12. When the pressure at gauge 84 rises and remains above 50 mmHg for 4 seconds, the test has passed and the system moves to a "PASSTHROUGH" state. (It should be noted that the system may alternatively pressurize the cavity and then detect whether the monitored pressure falls below a predetermined level within a predetermined time period, indicating that a perforation may be present.) As illustrated in FIG. 4, the "PASSTHROUGH" condition cannot be reached unless the body cavity assessment has been performed. In this capacity, the perforation detection system circuitry and logic components function as a pre-test lockout means.

In the "PASSTHROUGH" condition the $CO_2$ is turned off and the vacuum pump is re-enabled by re-opening valve 88.

If the ENABLE button 33 has been pressed (automatic mode), RF power 114 ("APPLY RF POWER") will be delivered automatically to the array 44 once the cavity assessment cycle has been completed and passed. If the ENABLE button has not been depressed (semiautomatic mode), the system moves through the "PASSTHROUGH" state and waits for footswitch actuation 112 ("WAIT FOR FOOTSWITCH"). The user must press the button to enable the RF generator and then press the foot switch 32 to deliver RF power 114.

In the event the cavity assessment test is not passed after the 30 second timer has expired, an audible tone sounds and visual indicators flash. The system remains in a TEST FAIL state, step 116, and awaits further action by the user. If the user presses the foot switch, the system re-sets to the initial ready state, step 108, with the $CO_2$ flow off. The user may attempt the cavity assessment sequence as many times as desired. As FIG. 4 illustrates, the perforation detection system circuitry and logic components function as a post-test lockout means preventing delivery of RF power using the ablation device if the body cavity assessment is run but not passed.

Alternatively, after one or more cavity assessment procedures has been performed and failed, the user may choose to activate a form of override means to override the post-test lockout means and cause the system to deliver RF energy despite the cavity assessment test having been failed. To do so, the user will press and hold the ENABLE button 33 for six seconds. Note that the pressure check must be attempted at least one time before this feature is available. If the user overrides the cavity assessment, the system moves to the "PASSTHROUGH" state to wait for footswitch step 112.

If at any time during the above sequence, the user should close the ablation device, a DC short will be detected in the electrode array by the RF generator's DC short detection circuitry. Closing the device causes the state of the perforation test to change to fail, and the system resets to the "WAIT FOR DEPLOY" state, step 106. The system will then require that cavity assessment be performed again once the array is reopened. This assures that the last step performed before the application of RF energy is the perforation detection test: if the user, after having successfully completing the test, decides to close and remove the device for any reason, the perforation detection test must be performed again once the device is deployed in the body cavity. This requirement also prevents a user from abusing the system by running cavity assessment with the device outside the body, and then inserting the device, overriding the test, and ablating without having ever performed cavity assessment within the body cavity.

For additional safety, the perforation detection system preferentially uses CO2, though other gases or liquids, such as normal saline, may be used. The pressure and flow limits follow well known guidance documents for insufflators. In the case of uterine perforation detection, the limits follow hysteroflator guidance documents. Though other configurations are possible, the cavity to be assessed should be in series between the source and pressure signal lines. In this manner, any kinked tubing or other problems will not lead to a false test result. Additionally, the system is capable of detecting perforations exceeding the range of sizes of devices normally inserted into body cavities (from say 15 mm down to less than 1 mm diameter).

In order to reliably detect perforations in uterine cavities, the pressure threshold in that case is preferentially kept below the average cracking pressure of the fallopian tubes.

There are several features that improve the system's ease of use. Firstly, the physician can start or stop the perforation test at any time in the sequence. Secondly microprocessor 34 is capable of distinguishing the difference between a device that is closed versus a device that is undergoing slight motion in the body cavity, thus reducing the likelihood that a passed test condition will be overturned. Finally, the system includes a collar assembly 63 in FIG. 2a which is capable of sealing the entry into the body cavity BC if leaks are determined to exist, thus reducing the likelihood of a false test failure.

Although the forgoing description is with reference to a perforation detection system having a device usable to ablate tissue within a uterus, the present invention is applicable to perforation detection within other body cavities, and to perforation detection systems having medical devices useful for procedures other than ablation. In addition, although the system is described with reference to a particular embodiment, many other configurations are suitable for implementing the teachings of the invention. Those having ordinary skill in the art will certainly understand from the embodiment disclosed herein that many modifications are possible without departing from the teachings hereof. All such modifications are intended to be encompassed within the following claims.

We claim:

1. A system for ablating tissue in a body cavity, the system including:
    a source of inflation medium;
    an ablation device insertable into a body cavity, the ablation device fluidly coupled to the source of inflation medium for delivery of inflation medium into the body cavity;
    a source of ablation energy coupled to the ablation device;
    a pressure sensor positioned to detect a pressure within the body cavity; and
    feedback means coupled to the pressure sensor to activate a notification signal to alert a user if the pressure detected by the pressure sensor fails to remain above a predetermined level within a predetermined amount of time.

2. The system of claim 1, wherein the feedback means is for activating an auditory notification signal.

3. The system of claim 2, further including:
    override means for permitting a user to treat a body cavity using the ablation device after the pressure sensor has been used to monitor for the presence of a perforation in the body cavity, and after the pressure monitored by the pressure sensor has failed to remain above the predetermined level within the predetermined amount of time.

4. The system of claim 1, wherein the feedback means is for activating a visual notification signal.

5. The system of claim 1, wherein the feedback means includes:
    electronics electronically coupled to the pressure sensor, the electronics configured to generate a feedback signal in the event the detected pressure fails to remain above a predetermined level within the predetermined amount of time; and
    a feedback device coupled to the electronics, the feedback device responsive to the feedback signal for alerting a user to the presence of a perforation in the body cavity.

6. The system of claim 5, further including:
    pre-test lockout means for preventing treatment of a body cavity using the ablation device until after the pressure sensor has been used to monitor for the presence of a perforation in the body cavity.

7. The system of claim 6 wherein the ablation device includes a closed position and an opened position, wherein the system includes means for detecting when the ablation device is in the closed position, and wherein the pre-test lockout means is further for preventing treatment of a body cavity using the ablation device until after the ablation device has been moved to an opened position and after the pressure sensor has been subsequently used to monitor for the presence of a perforation in the body cavity.

8. The system of claim 5, further including:

post-test lockout means for preventing treatment of a body cavity using the ablation device if the pressure monitored by the pressure sensor has failed to remain above the predetermined level within the predetermined amount of time; and override means for overriding the post-test lockout means, thereby permitting a user to treat a body cavity using the ablation device after the pressure sensor has been used to monitor for the presence of a perforation in the body cavity, and after pressure monitored by the pressure sensor has failed to remain above the predetermined level within the predetermined amount of time.

9. The system of claim 1, wherein the ablation device includes an ablation electrode.

10. The system of claim 9, wherein the energy source is a source of RF energy.

11. The system of claim 9 further including a vacuum source fluid coupled to the ablation device, the vacuum source operable during ablation using the ablation electrode.

12. The system of claim 1, wherein the ablation device includes one or more electrodes formed of metallized fabric mesh.

13. The system of claim 1, further including a vacuum source fluidly coupled to the ablation device.

14. The system of claim 1 wherein the ablation device is an RF ablation device.

15. The system of claim 1 wherein the ablation device is a thermal ablation device.

16. The system of claim 15 wherein the ablation device includes an ablation element fluidly coupled to a source of heated fluid.

17. The system of claim 1 wherein the ablation device includes an ablation element having a bicornal shape to approximate the interior shape of a uterus.

18. The system of claim 1 wherein the inflation medium is a gas.

19. The system of claim 18 wherein the gas is carbon dioxide.

20. The system of claim 1 wherein the inflation medium is a liquid.

21. The system of claim 20 wherein the liquid is saline.

22. The system of claim 1 wherein the system is for uterine ablation and wherein the predetermined level is selected to be below a cracking pressure for fallopian tubes.

23. The system of claim 1 further including a collar assembly on the ablation device for sealing an opening to the body cavity.

* * * * *